United States Patent
Yale

[11] 3,935,197
[45] Jan. 27, 1976

[54] 2-STYRYL-4H-PYRIDO(1,2-A)PYRIMIDIN-4-ONES

[75] Inventor: Harry L. Yale, New Brunswick, N.J.

[73] Assignee: E. R. Squibb & Sons, Inc., Princeton, N.J.

[22] Filed: May 16, 1975

[21] Appl. No.: 578,237

[52] U.S. Cl... 260/240 D; 260/251 A; 260/256.5 R; 260/240.9; 424/251
[51] Int. Cl.² .......................... C07D 239/70
[58] Field of Search...... 260/251 A, 240 D, 256.5 R

[56] References Cited
UNITED STATES PATENTS

| | | | |
|---|---|---|---|
| 3,585,198 | 6/1971 | Meszaros et al. | 260/251 A |
| 3,631,035 | 12/1971 | Cox | 260/240 D |
| 3,753,981 | 8/1973 | Breuer et al. | 260/240 D |

Primary Examiner—Arthur P. Demers
Attorney, Agent, or Firm—Lawrence S. Levinson; Merle J. Smith; Donald J. Barrack

[57] ABSTRACT

2-Styryl-4H-pyrido[1,2-a]pyrimidin-4-ones having the formula

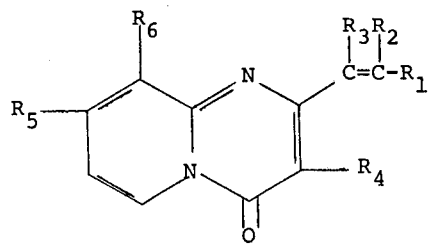

wherein $R_1$ is aryl; $R_2$ and $R_3$ are the same or different and are hydrogen or alkyl; and $R_4$, $R_5$ and $R_6$ are the same or different and are hydrogen or methyl, have useful hypotensive activity.

10 Claims, No Drawings

2-STYRYL-4H-PYRIDO(1,2-A)PYRIMIDIN-4-ONES

SUMMARY OF THE INVENTION

Styryl-4H-pyrido[1,2-a]pyrimidin-4-ones have been found to be useful hypotensive agents. The compounds of this invention have the formula

I

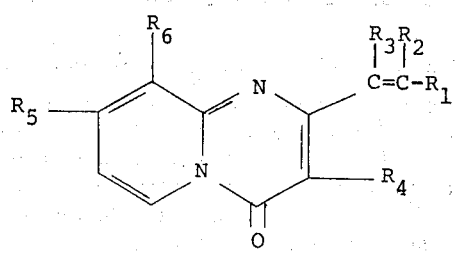

In formula I and throughout the specification the symbols are as defined below.

$R_1$ is phenyl, phenyl substituted with 1, 2 or 3 of the same or different alkyl, alkoxy or halogen groups, phenyl substituted with 1 or 2 trifluoromethyl groups (two dialkylamidosulfonyl or two trifluoromethyl groups cannot be ortho to each other);

$R_2$ is hydrogen or alkyl;
$R_3$ is hydrogen or alkyl;
$R_4$ is hydrogen or methyl;
$R_5$ is hydrogen or methyl; and
$R_6$ is hydrogen or methyl.

The term alkyl as used throughout the specification refers to alkyl groups having 1 to 4 carbon atoms, other than tertiary butyl.

The term alkoxy as used throughout the specification refers to groups having the formula $Y-O-$ wherein Y is alkyl as defined above.

The term halogen as used throughout the specification refers to chlorine, bromine, fluorine and iodine (chlorine and bromine are preferred).

DETAILED DESCRIPTION OF THE INVENTION

The 2-styryl-4H-pyrido[1,2-a]pyrimidin-4-ones of formula I are useful as hypotensive agents in mammalian species such as dogs, cats, etc., and can be administered in a daily dose of from about 5 to 50 milligrams/kilogram of animal body weight, preferably about 5 to 25 milligrams/kilogram of animal body weight, in single or divided doses.

The active compounds of the present invention are administered orally, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations may, of course, be varied and may conveniently be between about 5% and about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The compounds of formula I can be prepared from pyrido[1,2-a]pyrimidin-4-ones having the formula

II

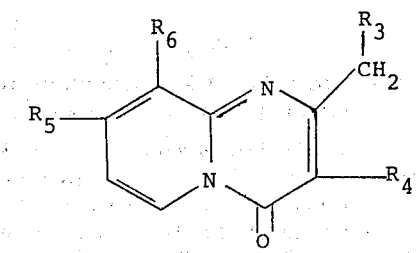

and aldehydes and ketones having the formula III

III 

The precursors of formulas II and III are reacted in a protic solvent, e.g., a lower alkanol such as methanol, in the presence of about one equivalent of a strong base, e.g., sodium methoxide. While reaction conditions are not critical, the reaction is a difficult one and will preferably be run at the reflux temperature of the solvent for extended periods of time.

The pyrido[1,2-a]pyrimidin-4-ones of formula II are known in the art; see, for example, U.S. Pat. No. 3,585,198 issued June 15, 1971.

Those compounds of formula I wherein $R_2$ is hydrogen or methyl are preferred, and those wherein $R_2$ is hydrogen are particularly preferred.

Those compounds of formula I wherein $R_3$ is hydrogen or methyl are preferred, and those wherein $R_3$ is hydrogen are particularly preferred.

The following examples are specific embodiments of this invention.

EXAMPLE 1 trans-9-Methyl-2-styryl-4H-pyrido[1,2-a]pyrimidin-4-one

To a solution of 1.1g of sodium methoxide and 25ml of absolute methanol is added 1.1g of 2,9-dimethyl-4H-pyrido-[1,2-a]pyrimidin-4-one, followed by 2.2g of benzaldehyde. The mixture is heated and stirred under reflux for 15 hours and concentrated on a rotary evaporator in vacuo at 45°C. The residual material is distributed between 100ml of chloroform and 50ml of water. The two solutions are separated and the chloroform solution is washed with saturated aqueous sodium chloride, dried, filtered, and the filtrate concentrated. The residual material is recrystallized from 100ml of cyclohexane to yield 0.44g of the title compound, melting point 150°–152°C.

EXAMPLE 2

9-Methyl-2-[2-(3,4,5-trimethoxyphenyl)ethenyl]-4H-pyrido-[1,2-a]pyrimidin-4-one.

To a solution of 2.2g of sodium methoxide in 100ml of absolute methanol is added 3.5g of 2,9-dimethyl-4H-pyrido-[1,2-a]pyrimidin-4-one, followed by 4.0g of 3,4,5-trimethoxybenzaldehyde. The mixture is stirred and heated under reflux for 28 hours. A crystalline solid separates and this is colled and filtered. The solid consists of a mixture of colorless and yellow crystals that are separated manually to give 1.52g of a pale yellow solid, melting point 208° – 210°C. The yellow solid is recrystallized from 35ml of methoxyethanol to yield 1.22g of the title compound, melting point 212°–214°C.

EXAMPLE 3

3,9-Dimethyl-2-[trans-2-(3,4,5-trimethoxyphenyl)ethenyl]-4H-pyrido[1,2-a]pyrimidin-4-one.

To a solution of 1.3g of sodium methoxide in 75ml of absolute ethanol is added 2.0g of 2,3,9-trimethyl-4H-pyrido-[1,2-a]pyrimidin-4-one, followed by 4.0g of 3,4,5-trimethoxybenzaldehyde. The mixture is stirred and heated under reflux for 89 hours. The reaction mixture is cooled, the solid is filtered, washed with 20ml of ether and 25ml of water, dried, and recrystallized from 75ml of acetonitrile to yield the title compound, melting point 218°–219°C dec.

EXAMPLE 4

2-[trans-2-(3,4,5-Trimethoxyphenyl)ethenyl]-4H-pyrido[1,2-a]-pyrimidin-4-one.

To a solution of 1.3g of sodium methoxide in 75ml of absolute ethanol is added 3.2g of 2-methyl-4H-pyrido[1,2-a]-pyrimidin-4-one, followed by 4.0g of 3,4,5-trimethoxyphenyl-benzaldehyde. The mixture is stirred and heated under reflux for 24 hours. The mixture is worked up as described in Example 3 to yield the title compound, melting point 212°–214°C, dec.

EXAMPLE 5

3,9-Dimethyl-2-[2-methyl-2-(3,4,5-trimethoxyphenyl)ethenyl]-4H-pyrido[1,2-a]pyrimidin-4-one To a solution of 1.3g of sodium methoxide in 75 ml of absolute methanol is added 2.0g of 2,3,9-trimethyl-4H-pyrido[1,2-a]pyrimidin-4-one, followed by 4.2g of 3,4,5-trimethoxyacetophenone. The mixture is stirred and heated under reflux for 97 hours to yield the title compound.

EXAMPLE 6

2-[(2-Ethyl-1-phenyl)ethenyl]-9-methyl-4H-pyrido[1,2-a]-pyrimidin-4-one

A.

9-Methyl-2-n-propyl-4H-pyrido[1,2-a]pyrimidin-4-one

A solution of 54.0g of 2-amino-3-methylpyridine, 144.0g of methyl butyrylacetate, 5.0g of p-toluenesulfonic acid, and 750ml of ethylene glycol monomethyl ether is heated in a nitrogen atmosphere, under reflux, for 60 hours. The solution is concentrated to dryness in vacuo, and the residual oil extracted with two 250ml portions of pentane. The pentane solution is concentrated to a volume of 250ml and cooled at −30°C to yield the title compound, melting point 59°–60°C.

B.

2-[(2-Ethyl-1-phenyl)ethenyl]-9-methyl-4H-pyrido-[1,2-a]pyrimidin-4-one

To a solution of 1.3g of sodium methoxide in 75ml of absolute ethanol is added 2.02g of 9-methyl-2-n-propyl-4H-pyrido[1.2-a)pyrimidin-4-one, followed by 2.12g of benzaldehyde. The mixture is stirred and heated under reflux for 75 hours to yield the title compound.

EXAMPLES 7–18

Following the procedure of Example 1, but substituting the compound shown in column I for 2,9-dimethyl-4H-pyrido-[1,2-a]pyrimidin-4-one and the compound shown in column II for benzaldehyde, yields the compound shown in column III.

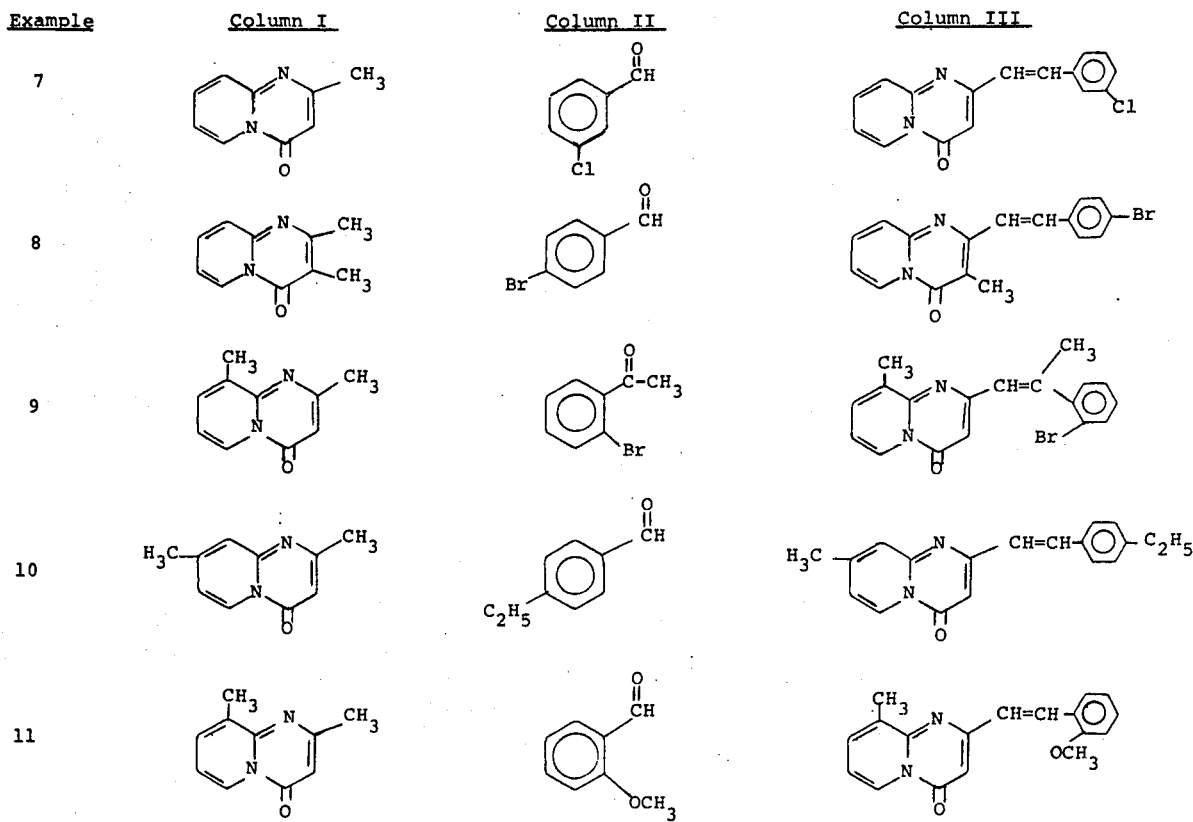

| Example | Column I | Column II | Column III |
|---|---|---|---|
| 12 | 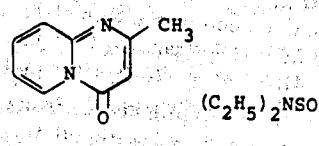 | 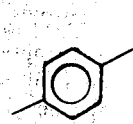 | 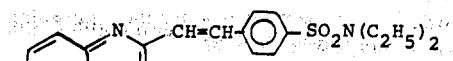 |
| 13 | 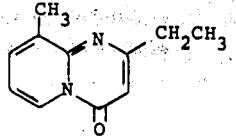 | 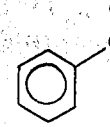 | 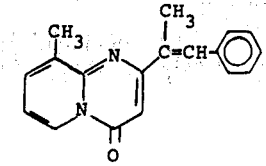 |
| 14 | 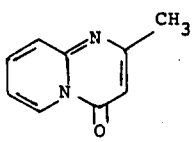 | 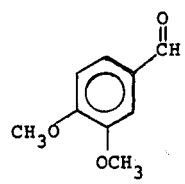 | 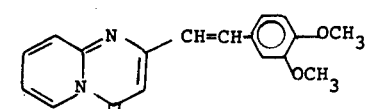 |
| 15 | 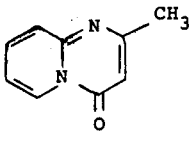 | 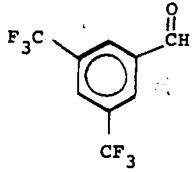 | 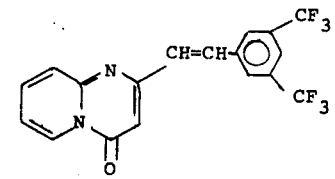 |
| 16 | 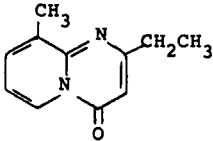 | 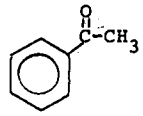 | 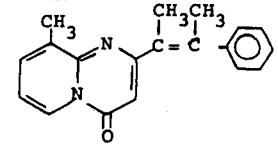 |
| 17 | 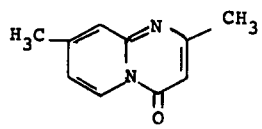 | 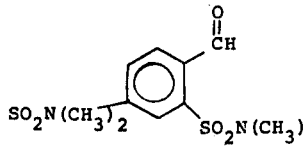 | 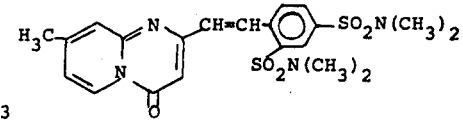 |
| 18 | 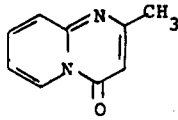 | 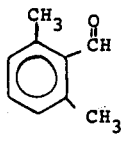 | 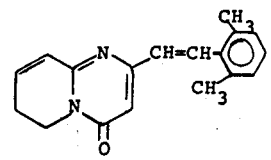 |
| 19 | 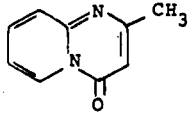 | 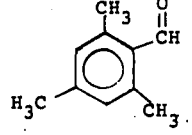 | 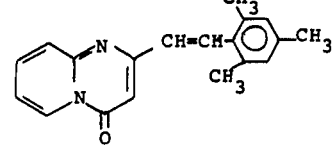 |
| 20 | 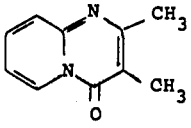 | 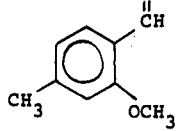 | 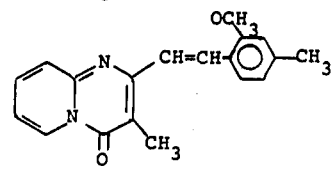 |

What is claimed is:
1. A compound having the formula

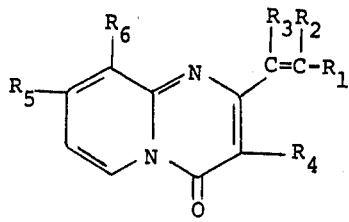

wherein $R_1$ is phenyl, phenyl substituted with 1,2 or 3 of the same or different alkyl, alkoxy or halogen groups, phenyl substituted with 1 or 2 dialkylamidosulfonyl groups, or phenyl substituted with 1 or 2 trifluoromethyl groups; $R_2$ and $R_3$ are the same or different and are hydrogen or alkyl; and $R_4$, $R_5$ and $R_6$ are the same or different and are hydrogen or methyl; and wherein the terms alkyl and alkoxy refer to non-tertiary groups having 1 to 4 carbon atoms.

2. A compound in accordance with claim 1 wherein $R_2$ and $R_3$ are hydrogen.

3. A compound in accordance with claim 1 wherein $R_6$ is methyl.

4. A compound in accordance with claim 3 wherein $R_4$ and $R_5$ are hydrogen.

5. A compound in accordance with claim 1 wherein $R_1$ is phenyl.

6. A compound in accordance with claim 1 wherein $R_1$ is 3,4,5-trimethoxyphenyl.

7. The compound in accordance with claim 1 having the name trans-9-methyl-2-styryl-4H-pyrido[1,2-a]pyrimidin-4-one.

8. The compound in accordance with claim 1 having the name 9-methyl-2-[2-(3,4,5-trimethoxyphenyl)ethenyl]-4H-pyrido[1,2-a]pyrimidin-4-one.

9. The compound in accordance with claim 1 having the name 3,9-dimethyl-2-[trans-2-(3,4,5-trimethoxyphenyl)-ethenyl]-4H-pyrido[1,2-a]pyrimidin-4-one.

10. The compound in accordance with claim 1 having the name 2-[trans-2-(3,4,5-trimethoxyphenyl)ethenyl]-4H-pyrido[1,2-a]pyrimidin-4-one.

* * * * *

UNITED STATES PATENT AND TRADEMARK OFFICE
CERTIFICATE OF CORRECTION

PATENT NO. : 3,935,197
DATED : January 27, 1976
INVENTOR(S) : Harry L. Yale

It is certified that error appears in the above—identified patent and that said Letters Patent are hereby corrected as shown below:

Column 1, line 23, after the number 2 please add --dialkyl-amidosulfonyl groups, or phenyl substituted with 1 or 2--.

Signed and Sealed this fourth Day of May 1976

[SEAL]

Attest:

RUTH C. MASON
Attesting Officer

C. MARSHALL DANN
Commissioner of Patents and Trademarks